(12) United States Patent
Hansen

(10) Patent No.: US 8,500,670 B2
(45) Date of Patent: Aug. 6, 2013

(54) POST-OPERATIVE VEST

(76) Inventor: Doris Hjorth Hansen, Chiaverano (IT)

( * ) Notice: Subject to any disclaimer, the term of this patent is extended or adjusted under 35 U.S.C. 154(b) by 12 days.

(21) Appl. No.: 13/164,033

(22) Filed: Jun. 20, 2011

(65) Prior Publication Data

US 2011/0251543 A1 Oct. 13, 2011

Related U.S. Application Data

(63) Continuation of application No. 10/536,815, filed as application No. PCT/IB03/06395 on Nov. 27, 2003, now abandoned.

(30) Foreign Application Priority Data

Nov. 29, 2002 (GB) .................................. 0227838.0

(51) Int. Cl.
| | |
|---|---|
| *A41D 1/04* | (2006.01) |
| *A41D 13/00* | (2006.01) |
| *A61F 5/37* | (2006.01) |
| *A61F 5/00* | (2006.01) |
| *A61F 13/00* | (2006.01) |
| *A61F 15/00* | (2006.01) |
| *A61F 13/06* | (2006.01) |
| *A61B 19/00* | (2006.01) |
| *A41C 3/00* | (2006.01) |
| *A61L 15/00* | (2006.01) |

(52) U.S. Cl.
USPC ............ 602/75; 2/92; 2/463; 2/913; 128/846; 128/869; 128/874; 128/875; 128/876; 450/1; 450/63; 602/19; 602/53; 602/60; 602/61; 602/76; 602/77; 602/78; 602/79

(58) Field of Classification Search
USPC .................. 602/19, 53, 60–61, 75–79; 450/1, 450/63; 128/846, 869, 874–876; 2/92, 93, 2/462, 463, 913
See application file for complete search history.

(56) References Cited

U.S. PATENT DOCUMENTS

| | | | |
|---|---|---|---|
| 2,800,902 A | 7/1957 | Wiltrout | |
| 3,400,710 A | 9/1968 | Goldstein | |

(Continued)

FOREIGN PATENT DOCUMENTS

| | | | |
|---|---|---|---|
| EP | 0 260 351 A1 | 3/1988 | |
| EP | 0 368 583 A1 | 5/1990 | |

(Continued)

OTHER PUBLICATIONS

May 22, 2003 Search Report for Great Britain Application No. GB 0227838.0 (1 page).

(Continued)

*Primary Examiner* — Patricia Bianco
*Assistant Examiner* — Brandon L Jackson
(74) *Attorney, Agent, or Firm* — Popovich, Wiles & O'Connell, P.A.

(57) ABSTRACT

The invention relates to a variable tension chest support for use by patients having undergone thoracic surgery. The chest support may be worn directly on the skin of a patient and comprises a band of stretchable material and one or more grips which are wholly or partially concealed within pockets with which the patient may alter the tension of the chest encircling band. The device allows a patient to modify the level of tension applied to the chest, thus managing the recovery process, while providing a basic level of support at all times the support is in use.

16 Claims, 2 Drawing Sheets

U.S. PATENT DOCUMENTS

| | | | |
|---|---|---|---|
| 3,968,803 | A | 7/1976 | Hyman |
| 4,022,197 | A | 5/1977 | Castiglia |
| 4,396,013 | A | 8/1983 | Hasslinger |
| D273,331 | S | 4/1984 | Gruber |
| 4,630,610 | A | 12/1986 | Fletcher |
| 5,152,741 | A | 10/1992 | Farnio |
| 5,411,461 | A | 5/1995 | Thomascik |
| 5,421,809 | A | 6/1995 | Rise |
| 5,503,620 | A | 4/1996 | Danzger |
| 5,527,270 | A | 6/1996 | Chase et al. |
| 5,538,502 | A | 7/1996 | Johnstone |
| 5,634,439 | A | 6/1997 | O'Brien |
| 5,664,257 | A * | 9/1997 | Hall .................... 2/69 |
| 5,843,008 | A | 12/1998 | Gerhard |
| 6,068,606 | A | 5/2000 | Castel et al. |
| 6,135,975 | A | 10/2000 | Johnstone |
| 6,240,564 | B1 | 6/2001 | Te Kanawa |
| 6,280,287 | B1 * | 8/2001 | Keith et al. .................... 450/1 |
| 6,296,618 | B1 | 10/2001 | Gaber |
| 6,431,947 | B1 | 8/2002 | Henz |
| 2001/0034498 | A1 | 10/2001 | Heyman et al. |

FOREIGN PATENT DOCUMENTS

| | | |
|---|---|---|
| GB | 1 054 741 A | 1/1967 |
| WO | WO 93/06936 A1 | 4/1993 |
| WO | WO 99/65428 A1 | 12/1999 |
| WO | WO 2004/049841 A2 | 6/2004 |

OTHER PUBLICATIONS

Jun. 14, 2004 Search Report for International Application No. PCT/IB03/06395 (5 pages).

* cited by examiner

POST-OPERATIVE VEST

CROSS-REFERENCE TO RELATED APPLICATIONS

This application is a continuation of U.S. patent application Ser. No. 10/536,815, filed Aug. 11, 2005, which is the National Stage Entry of PCT/IB03/06395, filed Nov. 27, 2003, which claims priority to United Kingdom Application No. 0227838.0, filed Nov. 29, 2002.

The present invention relates to providing chest support to patients having undergone invasive thoracic surgery. In particular, the present invention relates to a surgical chest support for patients having undergone surgery requiring opening of the chest cavity.

BACKGROUND OF THE INVENTION

Following thoracic surgery, for example open heart surgery, a patient normally suffers considerable pain caused by any movement of the chest, in particular when the patient breaths or coughs. Following the severe trauma of thoracic surgery, the ribs, sternum, and the muscles must be adequately supported in order to allow the region to heal. It is important, however, that the mobility of the chest is maintained and deep breathing and coughing are extremely important for the patient in order to both avoid lung infections and to aid in the healing process.

A number of devices have been employed to provide support for thoracic surgery patients. For example, rigid splints have been applied to the chest area, as have elasticated bandages. These devices have drawbacks such as the device does not allow the patient to breath freely or do not provide sufficient support. Furthermore, some prior art devices provide a fixed tension around the circumference of the chest. There are no provisions for varying the degree of tension in the supports. This is particularly important when the patient needs to cough or to perform a relatively strenuous movement. Patients are often inhibited from doing so as the severe trauma to the chest gives a feeling of weakness in the chest, and consequently contributes to the insecurity of the patient.

It would be desirable to provide a patient with a breathing support, the tension of which may be varied depending upon the requirements of the patient.

SUMMARY OF THE INVENTION

The present invention provides a post-operative chest support comprising a chest encircling band having at least a portion of stretchable material, characterised in that the band further comprises means for manually varying the tension of the band around the chest which are wholly or partially concealed within pockets.

The present invention overcomes the problems associated with the prior art as it provides a basic level of tension around the chest, providing constant support for a user. When further support is required, for example during coughing, deep breathing, or relatively strenuous movement by the patient, the patient may operate tension adjusting means in order to provide more support as required. Alternatively, where the wearer requires greater freedom of movement, the tension adjusting means may be operated by the user to reduce the tension applied to the chest. This approach is particularly advantageous as it allows patients to control the amount of tension applied to the chest and aids in managing their own recovery. It is important that breathing and coughing exercises are undertaken by a patient. Thus, it is particularly important that a patient has the ability to feel comfortable when carrying out such exercises.

It should be emphasized that the tension varying means referred to in the statement of invention are ones which may be adjusted easily when the support is being worn by the patient. The tension varying means are not intended to relate to any variation in the tension effected when initially closing the chest support, for example, adjusting the overlap of free ends of the chest support when fitting the device to a patient.

Preferably, the chest encircling band either comprises at least a portion of stretchable material, or more preferably, the band is substantially stretchable throughout its circumference. It is advantageous to provide a uniform encircling pressure of the chest. Preferably, this is provided by a chest encircling band having a substantially constant width. Preferably, the width is in the range of 5-40 cm. Preferably, the width of the band is sufficient to cover the length of the incision to the chest.

In use, the chest support applies a substantially constant (basic) tension to the patient's chest. This is modified depending on the force applied to the manual tension varying means.

In one preferred embodiment, the band forms part of a vest garment. This may be worn like a conventional vest by a user. The band may be permanently or removably attached to the vest, or formed integrally therewith.

Preferably, the chest encircling band is constructed, at least in part, from a flexible material, more preferably a stretchable fabric. Preferably the material can stretch up to 200% of its untensioned length, more preferably up to 100%, more preferably up to 50%, most preferably less than 20%, in particular 10% of its untensioned length. In a particularly preferred embodiment, "Millerighe" bandage material is used.

Since the chest support is preferably constructed from a flexible material and preferably lacks a mechanical moving part such as a pulley or other such drawstring elements for mechanically adjusting its tension or any other such skin irritating feature (e.g. a button, clip or a zip), the chest support is preferably non-irritating to the skin of a patient such that it can be worn directly on or next to the skin. The chest support is preferably sterile such that it can be applied to a patient in the operating room, preferably when the patient is awake.

Compared to the basic level of support applied to the chest of the patient, arbitrarily set at a pressure value of 1, the additional support which may be provided by actuating the manual tension varying means is preferably in the range of 1.01-5, more preferably 1.10-2.5, most preferably 1.25-1.75.

Millerighe comprises a mixture of polyester, polyamide, rubber and cotton and is preferably hypoallergenic. In a particularly preferred embodiment, the Millerighe has a compositional make up of about 51% polyester, 24% polyamide, 15% rubber, 10% cotton.

The chest encircling band may be continuous or may have attachment means at either end of the band. Preferably, the band comprises two ends having engagement means for securing the band around a patient's chest. The securing means may be in the form of complementary Velcro material attached to the ends of the band, clasps, buckles, buttons, and the like. Preferably the tension of the band is adjustable by the user or care helper by adjusting the basic tension applied to the band when first secured to the body of the user. This is most conveniently effected by having adjustable attachment means at the ends of the band. For example, Velcro is particularly advantageous as the initial tension can be altered depending on the degree of overlap of the ends of the band.

The chest encircling band, or material associated therewith, for example a vest garment, may be provided with anatomically compliant portions. For example, part of the band or associated material may have portions capable of supporting the patient's breasts.

Where the chest encircling band comprises a band having free ends which are wrapped around the body and secured to one another, the attachment may take place at any point around the patient's chest. Preferably, the attachment is either centrally behind the patient's body or to the side, for example, under the armpit.

Advantageously, the post-operative chest support of the present invention is provided with additional bands which may be slung over the shoulders of the user to provide support for the chest encircling band and to secure this in place around the user's body. These shoulder bands shall herein after be referred to as braces. These are preferably attached to the front and to the rear of the chest encircling band during wear. The braces may be permanently or removably attached to the chest encircling band or material associated therewith. The braces may be attached by Velcro or securing clips, buttons, clasps, and the like.

The manual tension varying means should be operable using the patient's hands or arms when the support is worn by the patient, i.e. in use. The manual tension varying means are preferably located towards the front of the chest encircling band when worn by the patient. The manual tension varying means should be permanently or removably attached to the chest encircling band. Preferably, the manual tension varying means comprise handles or grips which may be conveniently gripped and operated by a patient. Preferably, when the manual tension varying means cease to be operated by the patient, the band returns to its base tension, i.e. the tension applied to the chest when the band is secured to the patient.

In a particularly preferred embodiment, the chest encircling band has two handles mounted thereon. The patient can grip these handles and by pushing the handles together, the tension of the chest encircling band may be increased. Similarly, pulling the handles apart decreases the tension across the chest. The handles are located towards the front of the chest when the support is worn, and are preferably located in the range of 10-40 cm apart, more preferably 20-30 cm apart from one another.

The handles may be made from any suitable material, preferably a polymeric material. Particularly preferred materials are selected from polyetheretherketone, polysulphone, polyphenylenesulphone or polyethersulphone or similar material.

The manual tension varying means are preferably partially or fully enclosed. This may be effected by any suitable material. This allows the manual tension varying means to be partially or fully concealed discretely. For example, the support garment may comprise "pockets", resembling those found in many common garments. The handles may be concealed within these pockets such that they are not on general view. Alternatively, flaps or folds in the material may be used to conceal the manual tension varying means.

It is important that the vest is fixed on the chest in a comfortable manner, with minimal inhibition of breathing. The patient (or carer) should arrange the vest around the chest and close it in the exhaling phase, without stretching, but merely closing the vest, for example, folding the complementary velcro tabs over each other to fixate the support. This means that when the patient inhales (the thoracic cavity moves up and outwards), the support device gives the patient extra support and feeling of support needed to feel comfortable in the postoperative period. When coughing or breathing deeply the patient grips the two handles, which are fixed at the front with one or both hands. This means that the patient is in control of the degree of tension applied to the chest assuring the tension to be within the comfortable range for the patient.

Generally minimal pressure is applied to the patient's chest after open heart or thoracic surgery, which is why it is important the stress to remain within the comfort zone for the patient by only "folding" the vest around the chest in the exhaling phase. The purpose is to make the patient feel more comfortable and thereby lessen the pain.

The invention will now be described with reference to the drawings.

DETAILED DESCRIPTION OF THE INVENTION

Figure 1:
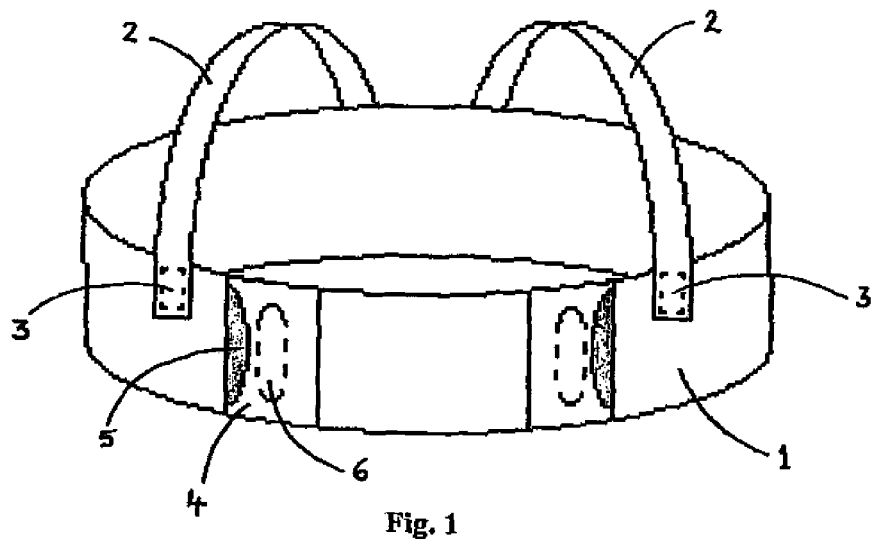
FIG. 1 shows a perspective view of the post-operative chest support of the present invention.

FIG. 1. shows a perspective view of the post-operative chest support of the present invention. The support comprises a chest encircling band 1 constructed of "Millerighe" bandage material. The band is shown in a closed position, as it would be worn around the chest of a user. Braces 2 are fixed to the rear of the band and are securely stitched in place. The braces are removably attached towards the front of the band (from the wearer's point of view) by Velcro strips 3. The external surface of the band, i.e. the surface not in contact with the chest of the user, has pockets 4 which are attached to the band 1 and have an opening 5 for the user's hand to enter and grip the handle 6. The handle 6, shown by hash lines, is concealed from general view within the pocket 4.

Figure 2:
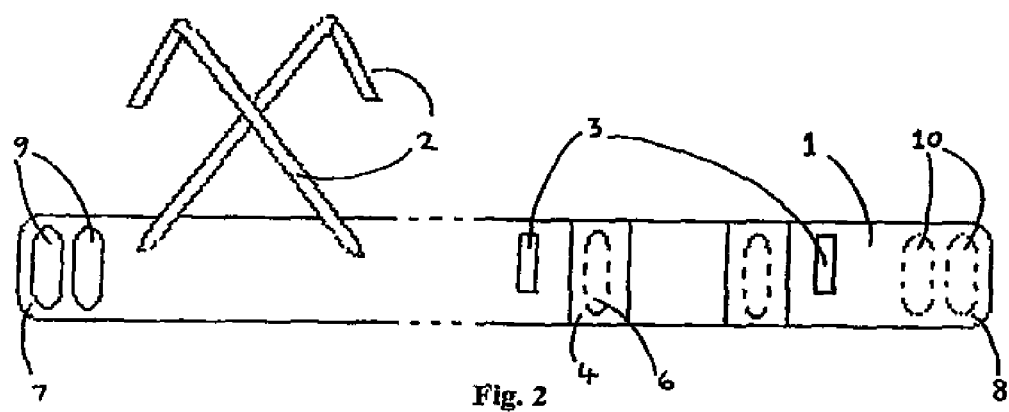
FIG. 2 shows the post-operative chest support of the present invention prior to its closure around the chest of a patient.

FIG. 2 shows the post-operative support in an open configuration, i.e. not worn by a patient. The band 1 has two free ends 7 and 8 bearing complimentary Velcro strips 9 and 10 for securing the band around the chest of the user. The overlap of the free ends may be adjusted to change the base tension of the band around a patient. The braces are shown in an open configuration. In use, once the band has been secured around the chest of the patient, the braces are brought over the shoulder and the free ends of the braces are brought into engagement with strips of Velcro complimentary to those borne on the free ends of the braces.

Figure 3:
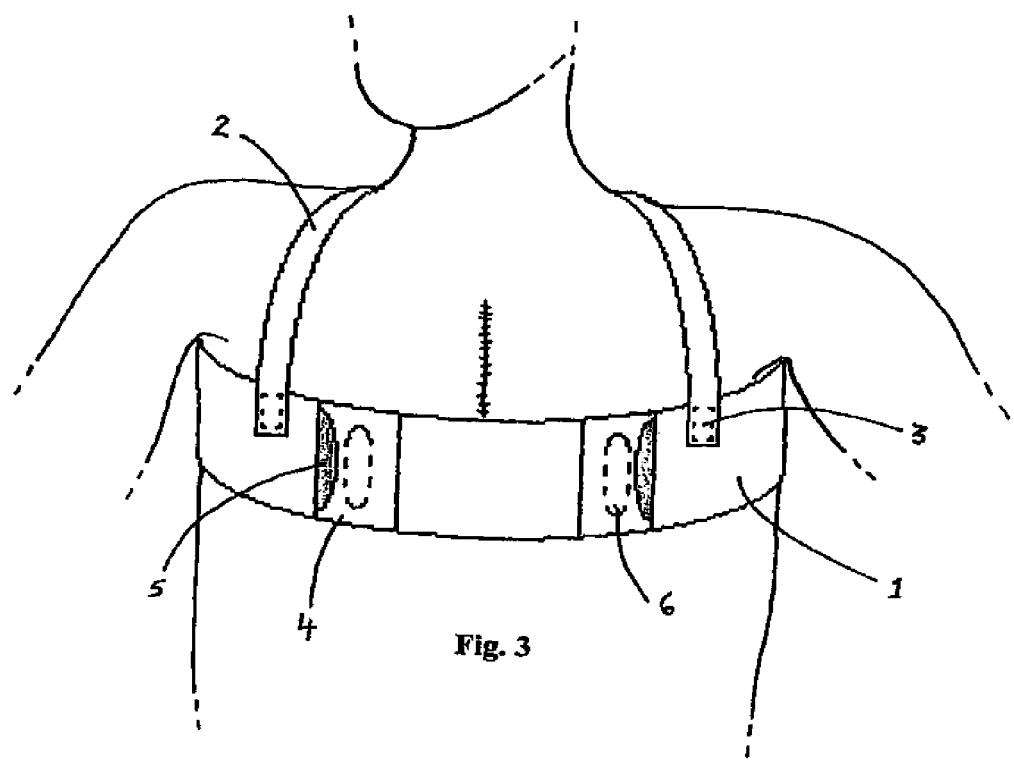
FIG. 3 shows the post-operative chest support of the present invention when worn by a patient.

FIG. 3 shows the post-operative chest support of the present invention in use with a patient. The band is secured around the chest and the braces secured over the shoulders, thus retaining the vest in an optimum position around the patient's chest. The patient can raise his hands to the handles 6 within the pockets 4 through the pocket openings 5, and by pushing his hands towards one another can tighten the band around the chest, thus increasing the tension applied to the chest.

What is claimed is:
1. A post-operative chest support for a patient comprising:
a chest encircling band of stretchable material having a substantially constant width, the chest encircling band having a securing system for securing the band about the patient's chest, the securing system fixing a uniform chest encircling pressure applied to the patient's chest at a first base uniform chest encircling pressure when the chest encircling band is secured about the patient's chest; and first and second pressure adjusting members attached on a front surface of the chest encircling band at a location that is accessible to the patient when the chest encircling band is secured about the patient's chest, the first and second pressure adjusting members being spaced apart a first distance when the first base uniform chest encircling pressure is applied to the patient's chest, the spacing between the first and second pressure adjusting members being adjustable upon application of external force by the patient from the first distance to a second distance and from the first distance to a third distance, the chest band applying a second uniform chest encircling pressure to the patient's chest when the first and second pressure adjusting members are spaced apart the second distance, the second uniform chest encircling pressure being greater than the first base uniform chest encircling pressure, the chest band applying a third uniform chest encircling pressure to the patient's chest when the first and second pressure adjusting members are spaced apart the third distance, the third uniform chest encircling pressure being less than the first base uniform chest encircling pressure.

2. The post-operative chest support of claim 1 wherein the stretchable material has an untensioned length and wherein the stretchable material has a maximum tensioned length that is less than 20% greater than the untensioned length.

3. The post-operative chest support of claim 2 wherein the maximum tensioned length is about 10% greater than the untensioned length.

4. The method of claim 2 further comprising:
manipulating the first and second pressure adjusting members to adjust the spacing between the first and second pressure adjusting members to a third distance which is greater than the first distance, the chest band applying a third pressure to the patient's chest when the first and second pressure adjusting members are spaced apart the third distance, the third pressure being less than the first base pressure.

5. The method of claim 4 wherein the securing system comprises hook-and-loop fasteners.

6. The method of claim 4 wherein the stretchable material has an untensioned length and wherein the stretchable material has a maximum tensioned length that is less than 20% greater than the untensioned length.

7. The method of claim 6 wherein the maximum tensioned length is about 10% greater than the untensioned length.

8. The method of claim 2 wherein the chest band includes a securing system.

9. The method of claim 8 wherein the chest band further comprises first and second pockets sized to receive the first and second handles.

10. The method of claim 2 wherein:
the chest band further comprises first and second shoulder straps mounted on the chest band.

11. The method of claim 2 wherein the first and second pressure adjusting members comprise first and second handles.

12. The post-operative chest support of claim 1 wherein the first and second pressure adjusting members comprise first and second handles.

13. The post-operative chest support of claim 12 wherein the chest encircling band further comprises first and second pockets sized to receive the first and second handles.

14. The post-operative chest support of claim 1 further comprising:
first and second shoulder straps mounted on the chest encircling band.

15. The post-operative chest support of claim 1 wherein the securing system comprises hook-and-loop fasteners.

16. A method of adjusting the pressure applied to a patient's chest following surgery comprising:
positioning a post-operative chest encircling support band of stretchable material across the chest of the patient at a time when the patient has exhaled to expel air from the patient's lungs to apply pressure to the patient's chest at a first base pressure, the chest band including first and second pressure adjusting members attached on a front surface of the chest band, the first and second pressure adjusting members being positioned to be accessible to the patient and being spaced apart a first distance from one another when the chest band applies the first base pressure to the patient's chest; and
manipulating the first and second pressure adjusting members to adjust the spacing between the first and second pressure adjusting members to a second distance which is less than the first distance, the chest band applying a second pressure to the patient's chest when the first and second pressure adjusting members are spaced apart the second distance, the second pressure being greater than the first base pressure.

\* \* \* \* \*